(12) United States Patent
Kandel et al.

(10) Patent No.: US 7,277,172 B2
(45) Date of Patent: Oct. 2, 2007

(54) MEASURING OVERLAY AND PROFILE ASYMMETRY USING SYMMETRIC AND ANTI-SYMMETRIC SCATTEROMETRY SIGNALS

(75) Inventors: Daniel Kandel, Aseret (IL); Kenneth P. Gross, San Carlos, CA (US); Michael Friedmann, Mountain View, CA (US); Jiyou Fu, Sunnyvale, CA (US); Shakar Krishnan, Santa Clara, CA (US); Boris Golovanevsky, Haifa (IL)

(73) Assignee: KLA-Tencor Technologies, Corporation, Milpitas, CA (US)

( * ) Notice: Subject to any disclaimer, the term of this patent is extended or adjusted under 35 U.S.C. 154(b) by 0 days.

(21) Appl. No.: 11/325,872

(22) Filed: Jan. 4, 2006

(65) Prior Publication Data

US 2006/0274310 A1 Dec. 7, 2006

Related U.S. Application Data

(60) Provisional application No. 60/687,951, filed on Jun. 6, 2005.

(51) Int. Cl.
 *G01J 4/00* (2006.01)
 *G01N 21/86* (2006.01)
(52) U.S. Cl. .................... 356/369; 250/559.09
(58) Field of Classification Search ............... 356/369; 250/559.09, 559.22
 See application file for complete search history.

(56) References Cited

U.S. PATENT DOCUMENTS 5,416,588 A  5/1995  Ducharme et al.
5,608,526 A  3/1997  Piwonka-Corle et al.
6,483,580 B1 * 11/2002  Xu et al. ................ 356/300
6,982,793 B1  1/2006  Yang et al.
2003/0002043 A1  1/2003  Abdulhalim et al.

OTHER PUBLICATIONS

TDB, "Mask Overlay Determination" IBM Technical Disclosure Bulletin, Dec. 1978, pp. 272-2773. www.delphion.com.
TDB, "Phase-Sensitive Overlay Analysis Spectrometry," IBM Technical Disclosure Bulletin, Mar. 1990. pp. 170-174 www.delphion.com.
TDB, Interferometric Method of Checking the Overlay Accuracy in Photolitho Graphic Exposure Processes.

* cited by examiner

*Primary Examiner*—Roy M. Punnoose
(74) *Attorney, Agent, or Firm*—Beyer Weaver LLP (57) ABSTRACT

Systems and methods are disclosed for using ellipsometer configurations to measure the partial Mueller matrix and the complete Jones matrix of a system that may be isotropic or anisotropic. In one embodiment two or more signals, which do not necessarily satisfy any symmetry assumptions individually, are combined into a composite signal which satisfies a symmetry assumption. The individual signals are collected at two or more analyzer angles. Symmetry properties of the composite signals allow easy extraction of overlay information for any relative orientation of the incident light beam with respect to a 1D grating target, as well as for targets comprising general 2D gratings. Signals of a certain symmetry property also allow measurement of profile asymmetry in a very efficient manner. In another embodiment a measurement methodology is defined to measure only signals which satisfy a symmetry assumption. An optional embodiment comprises a single polarization element serving as polarizer and analyzer. Another optional embodiment uses an analyzing prism to simultaneously collect two polarization components of reflected light.

27 Claims, 9 Drawing Sheets

MEASURING OVERLAY AND PROFILE ASYMMETRY USING SYMMETRIC AND ANTI-SYMMETRIC SCATTEROMETRY SIGNALS

CROSS REFERENCE TO RELATED PATENT APPLICATION

This application claims priority of U.S. Provisional Patent Application No. 60/687,951 filed 6 Jun. 2005 by Daniel Kandel et al., which application is incorporated herein by reference in its entirety for all purposes.

FIELD OF INVENTION

The invention pertains in general to scatterometry, and in particular to measuring overlay error and profile asymmetry using symmetric and anti-symmetric scatterometry signals.

BACKGROUND OF THE INVENTION

Scatterometry is currently used in the semiconductor industry to measure thickness and optical properties of thin films as well as the critical dimension (CD) and profile shape of periodic structures on a semiconductor wafer. Scatterometry is also perceived as a possible future technology for overlay error metrology for the 32 nm technology node and beyond. In principle, scatterometry has clear advantages over the current imaging technology of overlay metrology. Scatterometry is capable of measuring device-size structures which cannot be resolved by imaging. Scatterometry is also thought to be more robust to process variations and asymmetry in the profile of the measured structure. Apparatus and methods for measuring overlay error using scatterometry are described in U.S. patent application Ser. No. 10/729,838, entitled "Apparatus and Methods for Detecting Overlay Errors Using Scatterometry" and filed on Dec. 5, 2003, which is herein incorporated by reference.

The most prevailing methods for measuring profile asymmetry are critical dimension scanning electron microscopy (CD-SEM) and scatterometry. The CD-SEM approach is very slow and expensive. The current implementation of scatterometry CD metrology, which is also suitable for monitoring properties of the profile (including profile asymmetry), relies on detailed modeling and is therefore also rather slow. In addition, it is very difficult to accurately model complicated profiles, such as two gratings (one on top of the other) separated by a layered possibly non-flat film. Such structures reflect the structure of devices more accurately than the single-layer grating used for scatterometry CD metrology.

Scatterometry measurements can be carried out in unpolarized reflectometry mode or in ellipsometry mode, as described in U.S. patent application Ser. No. 10/729,838. In both cases, overlay information is extracted without any need for modeling, which makes scatterometry overlay metrology very efficient (relative to scatterometry CD metrology). The ellipsometry measurement contains detailed information about the polarization of light, which is absent from the unpolarized reflectometry measurement. This additional information contained in the ellipsometry signal can result in a higher sensitivity to overlay errors and, thus, gives this technique a significant advantage over unpolarized reflectometry. The question, however, is how to extract the overlay information encoded in the ellipsometry signal. Previous approaches to using scatterometry to measure overlay error rely on a particular symmetry property of the ellipsometry signal; i.e. that the signal is an even function of the overlay. In our terminology, ellipsometry signals which posses this property are symmetric signals. Not all ellipsometry signals are symmetric. For the simple case of a one-dimensional (1D) grating target with the incident beam of light perpendicular to the grating lines (hereinafter referred to as the "Azimuth-0" case), all ellipsometry signals are symmetric. For other cases of general relative orientation between the incident light and the grating lines (conical diffraction), some ellipsometry signals are asymmetric. For these cases a methodology has to be defined which allows measurements of signals of a well defined symmetry.

Accordingly, what is desired is an ellipsometry or more generally scatterometry method for extracting overlay information for any relative orientation of the incident light beam with respect to a 1D grating target (conical diffraction), as well as for targets comprising general 2D gratings.

SUMMARY OF THE INVENTION

Systems and methods are disclosed for using the signals produced by an ellipsometer to determine the overlay error between two layer structures on a specimen, such as a semiconductor wafer, while accounting for any asymmetries in the produced signals. In one embodiment two or more signals, which do not necessarily satisfy any symmetry assumptions individually, are combined into a composite signal which satisfies a symmetry assumption. The individual signals are collected at two or more analyzer angles. Symmetry properties of the composite signals allow easy extraction of overlay information for any relative orientation of the incident light beam with respect to a 1D grating target, as well as for targets comprising general 2D gratings. In another embodiment, a measurement methodology is defined to measure only signals which satisfy a symmetry assumption. An optional embodiment comprises a single polarization element serving as polarizer and analyzer. Another optional embodiment uses an analyzing prism to simultaneously collect two polarization components of reflected light. In an alternative embodiment, an elipsometer is used to obtain measurements from a structure, and these measurements are combined into an anti-symmetric signal that is then used to determine a profile asymmetry degree of the structure.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION OF THE INVENTION

Reference will now be made in detail to a particular embodiment of the invention, examples of which are illustrated in the accompanying drawings. While the invention will be described in conjunction with the particular embodiments, it will be understood that it is not intended to limit the invention to the described embodiments. To the contrary, it is intended to cover alternatives, modifications, and equivalents as may be included within the spirit and scope of the invention as defined by the appended claims.

The present invention introduces a system and method for combining information from one or more ellipsometry signals in a manner which allows easy extraction of overlay information for any relative orientation of the incident light beam with respect to a 1D grating target, as well as for targets comprising general 2D gratings. In addition, the disclosed analysis of the ellipsometry signal yields qualitative information about the profile of the grating. The degree of asymmetry of the profile can be easily inferred without additional measurements and with very little modeling. It is possible to use this profile information in order to decouple, to a certain extent, the overlay measurement from the properties of the profile. This desirable capability is absent from previous methods of overlay metrology (imaging and scatterometry), and may also serve to improve the efficiency of scatterometry CD applications.

Overlay Targets

Figure 1:
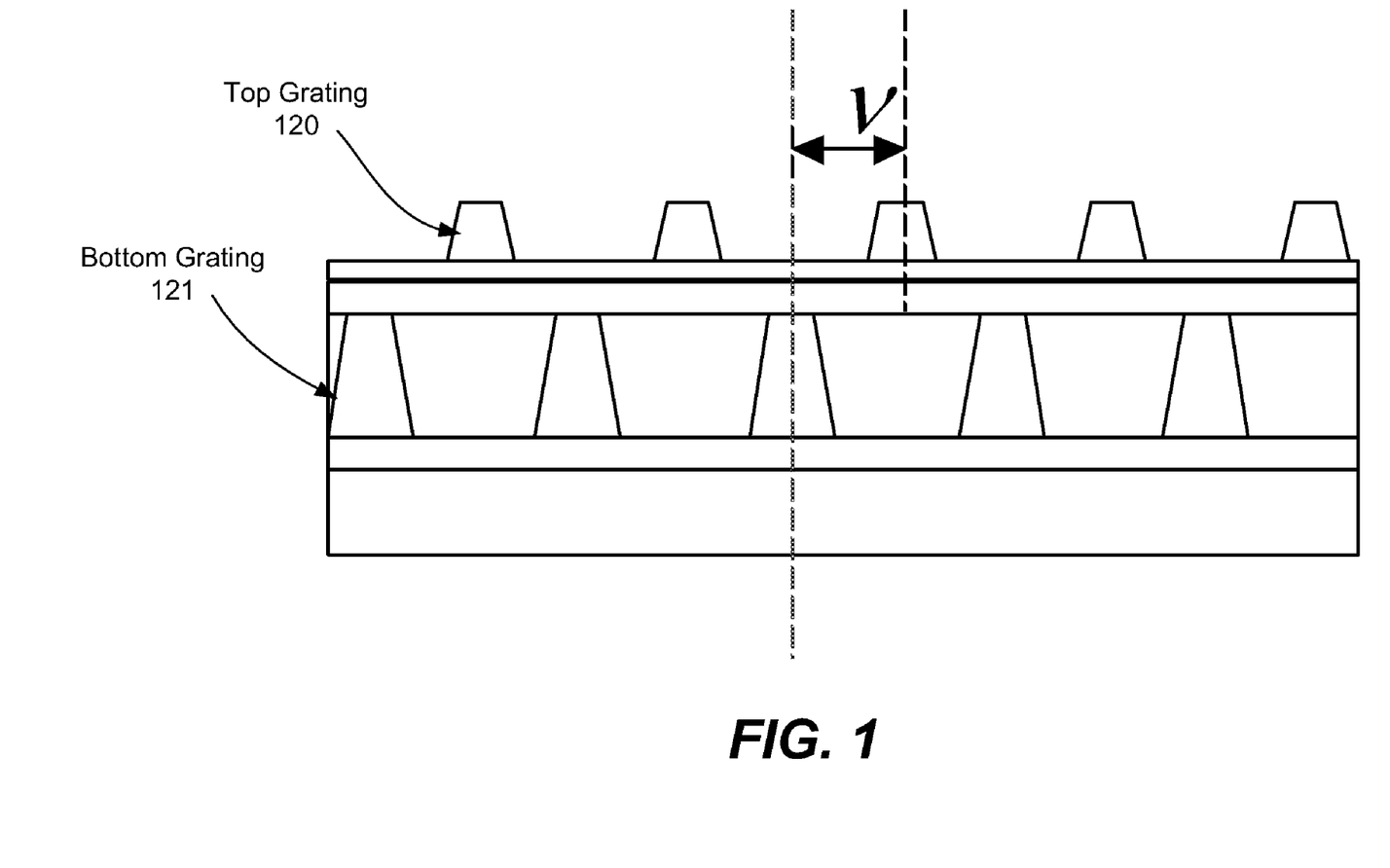
FIG. 1 is a diagram illustrating an exemplary overlay target, in accordance with an embodiment of the present invention.

An overlay target comprises one or more cells. Each cell comprises two largely overlapping gratings, each of which is in a different layer of the wafer. The two layers comprising the gratings may be separated by one or more intervening films, which may be patterned or unpatterned. The two gratings are referred to as the top and bottom gratings, and the overlay information refers to the shift between the top and bottom gratings. An exemplary overlay target is illustrated in FIG. 1, in accordance with an embodiment of the present invention. The top grating 120 and the bottom grating 121 are shifted relative to each other by an overlay amount denoted as v.

Disclosed herein are techniques for determining the shift between a top grating and a bottom grating in an overlay target by scattering light off of the overlay target, measuring the intensity of the scattered light, and then analyzing the scattered light to then determine overlay. One approach is to scatter unpolarized light, producing a single measured quantity per scattering measurement. A second approach is to scatter polarized light, producing more than one measured quantity per scattering measurement. An advantage of using polarized light is the larger number of available signals, producing a larger amount of measurement information and, due to a decrease in random errors in measurement, generally resulting in higher measurement precision. Another advantage of using polarized light is that under some conditions, the sensitivity of polarized light to the overlay is significantly higher than the sensitivity of unpolarized light. Embodiments of the present invention use polarized light in an ellipsometry setting.

Overlay targets are constructed in such a way that a rotation of the target by 180° results in a target which differs from the unrotated target only in the sign of the shift v between the top and bottom gratings. While in general the received signal is dependent on the shift v, algorithms used in current scatterometry overlay applications assume that all scatterometry signals, regardless of whether polarized or unpolarized light is used, are even functions of the shift, i.e. that the signals are independent of the sign of the shift v. Hereinafter, even functions of the shift v are referred to as "symmetric" functions. In the case of a symmetric signal, the invariance of the signal under 180° rotation allows easy extraction of the overlay from the measurement.

Similar to the general scatterometry case, in an ellipsometry setting it is desirable to use some assumption about the symmetry of the signal when the sign of the overlay v is changed, since without symmetry assumptions we are generally left with more resource-intensive choices, such as detailed modeling and/or simulating the complex target structure under inspection, in order to obtain overlay information with sufficient accuracy (for example with sub-nanometer accuracy). However, while it is desirable to use symmetry assumptions in ellipsometry applications, the assumption of symmetric signals holds for the azimuth-0 case but not for the general grating case. As mentioned above, an azimuth-0 case generally refers to a one-dimensional (1D) grating target with the incident beam of light perpendicular to the grating lines, while a "general grating" case refers to either a 1D or 2D grating target having an incident beam that is not limited to be perpendicular to grating lines. Accordingly, embodiments of the present invention relate to ellipsometry systems and methods for the extraction of overlay information for the general grating case, without any cost in target size, MAM time or algorithmic complexity. A basic idea of embodiments of the present invention is to take two or more signals which do not necessarily satisfy any symmetry assumptions individually, and combine them into a composite signal which satisfies a symmetry assumption.

The total offset v of a cell is the sum of two contributing factors: an intentional offset and an overlay (if present). The intentional offset is designed into the cell, and the overlay is an unknown quantity to be determined. Note that any symmetry of collected signals is with respect to the sign of the total offset v. Hence, in preparation for an ellipsometry measurement according to an embodiment of the present invention, a target is designed to comprise a plurality of cells, each of which has an intentional offset contributing to its total offset.

In one example embodiment of the present invention, measurements are taken on four cells. Four signals are collected from the four cells, and the collected signals are paired to generate a total of two difference signals: one between the first two cells and another between the second two cells. Finally, comparing the two differences determines the target overlay v. Of course, any suitable number of cells may be utilized in the present invention, depending on the level of precision required and the amount of target real estate available.

A Measurement System

Figure 2A:
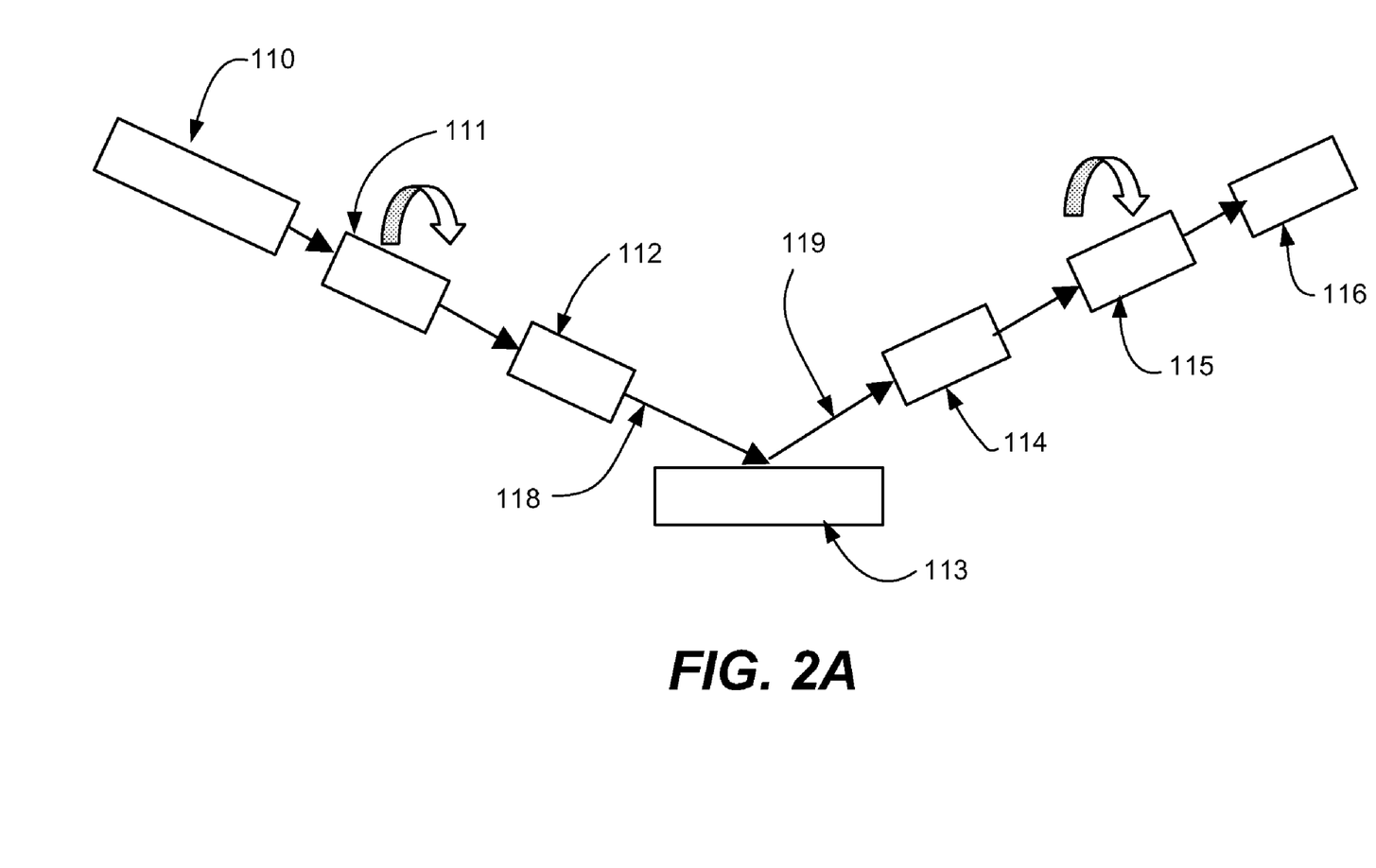
FIG. 2A is a diagram illustrating an ellipsometry system, in accordance with an embodiment of the present invention.

FIG. 2A is a diagram illustrating an ellipsometry system, in accordance with an embodiment of the present invention. The system comprises a polarizer referred to as the "Polarizer" 111 on the illumination side, and a polarizer referred to as the "Analyzer" 115 on the collection side. The Polarizer 111 rotates continuously. The Analyzer 115 may rotate or may be adjusted to specific angles. The Polarizer 111 and Analyzer 115 may be rotated with the help of one or more motors, such as stepper motors or servo motors. The ellipsometry system shown is referred to as a "Rotating Polarizer, Rotating Analyzer" (RPRA) ellipsometry system. Incident light 118 emitted from light source 110 travels through the rotating Polarizer 111 and focusing optics 112, and is scattered by sample 113. In the present description, the sample 113 generally comprises a semiconductor wafer comprising one or more overlay targets. Interaction of the light with an overlay target 113 modifies the state of polarization of the light. The scattered light 119 travels through collection optics 114 and rotating analyzer 115, and is detected by detector 116. Note that rotating quarter wave plates can be used instead of the Analyzer 111 and Polarizer 115.

Figure 2B:
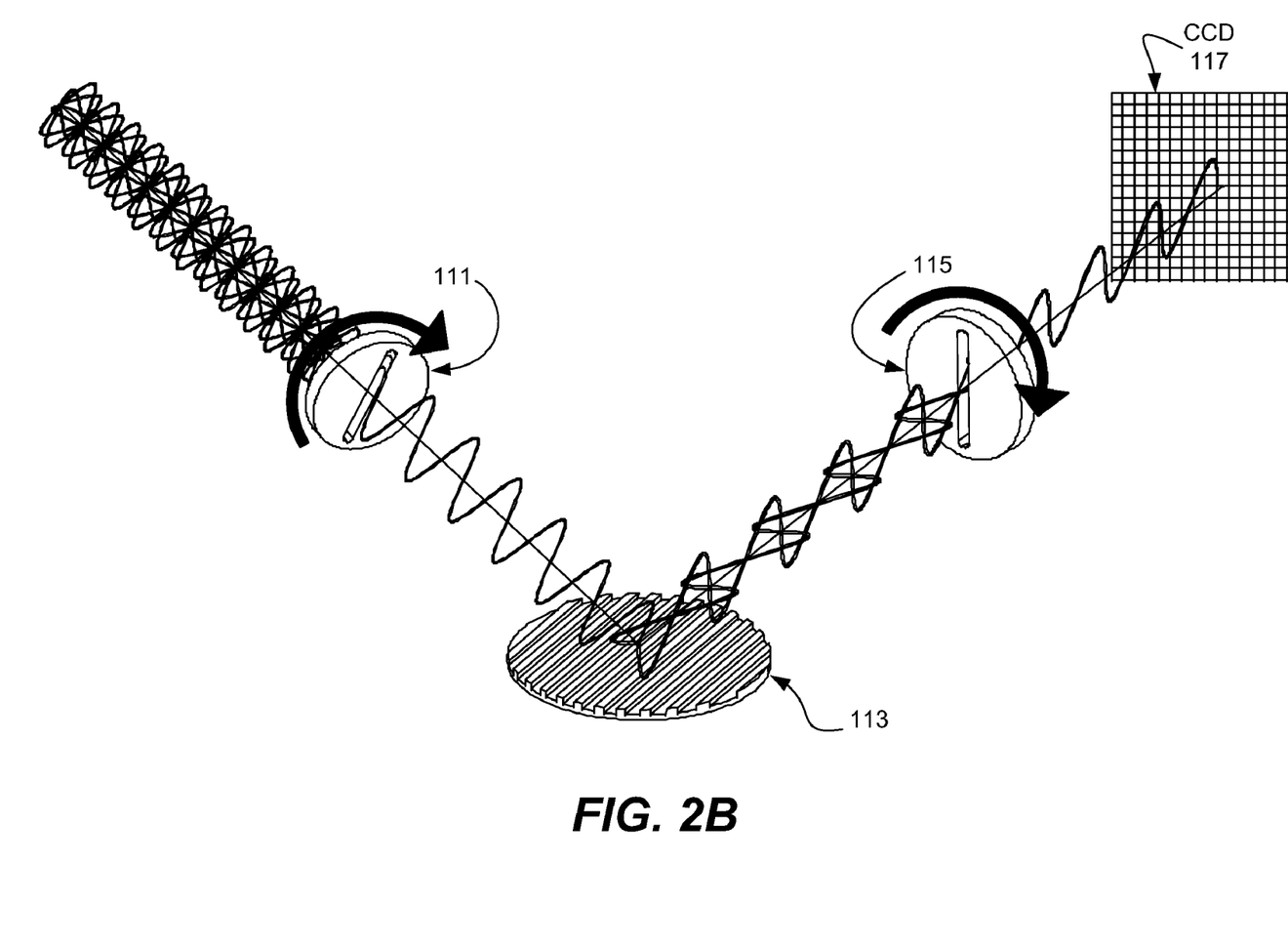
FIG. 2B is another diagram illustrating a rotating polarizer rotating analyzer configuration, in accordance with an embodiment of the present invention.

FIG. 2B is another diagrammatic representation of an RPRA configuration, showing the change in the state of light polarization before and after reflection by the sample 113, and showing a charge-coupled device (CCD) 117 for detecting the reflected light, in accordance with an embodiment of the present invention. Note that the above ellipsometry configurations are exemplary, and in general the ellipsometry configuration can be any of the configurations described in the U.S. patent application Ser. No. 10/729,838, which is incorporated herein by reference, with a modification of the setup of the polarization analyzer. Modification of the analyzer setup may be accomplished by firmware modification of the controller of the analyzer motor. Note that the RPRA ellipsometry system can be used to measure overlay of multiple layers, for example after each lithography step. Additionally, several other variations of the ellipsometry configuration are described below.

Figure 3:
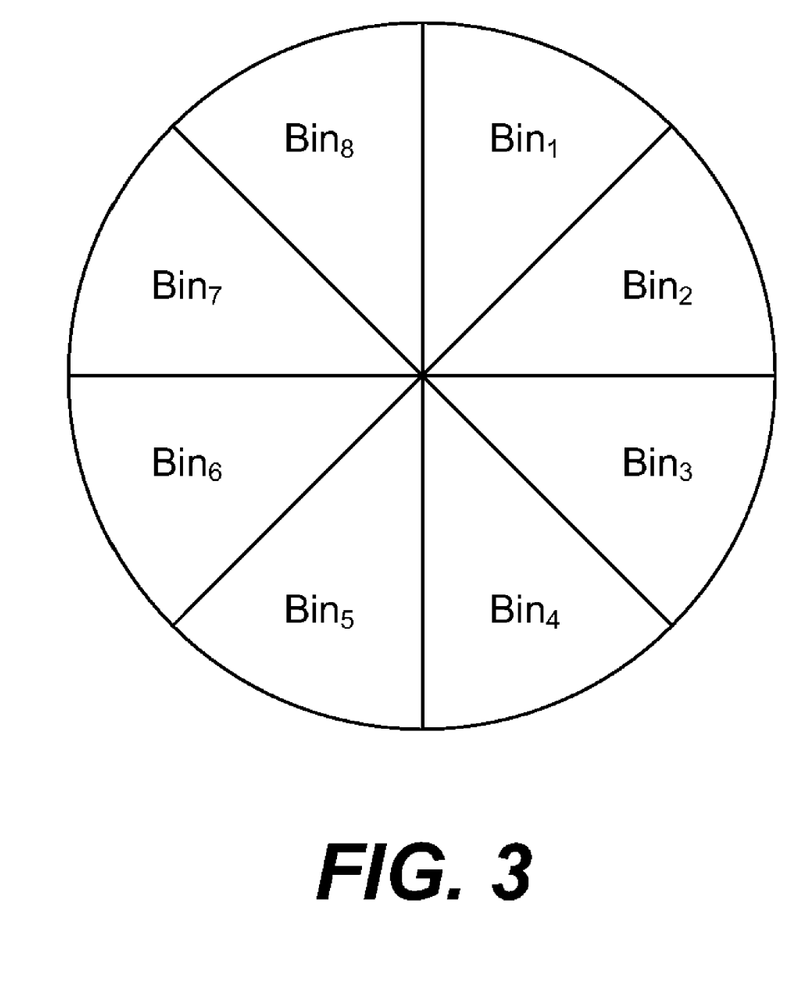
FIG. 3 shows a diagrammatic representation of an exemplary set of eight collection bins encompassing the rotation range of the Polarizer, in accordance with an embodiment of the present invention.

While the Polarizer 111 rotates continuously, signals collected on the Analyzer 115 side are binned over the rotation range of the Polarizer 111. For example, the collected signals can be binned into 8 bins, as shown in FIG. 3, with each bin comprising 45° of the total 360° rotation range of the Polarizer 111. The binned quantities are then combined, as described below, to form one or more composite signals having desired symmetry properties.

For example, in the exemplary embodiment using 8 bins with the Analyzer 115 set to an angle A, a total of 8 quantities $S_1(A), \ldots, S_8(A)$ are collected, each quantity $S_i(A)$ representing the total intensity of bin i at Analyzer 115 angle A. The collected quantities allow the extraction of a total of 3 independent quantities, herein referred to as $I_0(A)$, $\alpha(A)$ and $\beta(A)$, each given as a function of the 8 collected "raw" quantities $S_1(A), \ldots, S_8(A)$ as follows:

$$I_0 = \frac{S_1 + S_2 + S_3 + S_4 + S_5 + S_6 + S_7 + S_8}{2\pi},$$

$$\alpha = \frac{S_1 - S_2 - S_3 + S_4 + S_5 - S_6 - S_7 + S_8}{4I_0}$$

and $$\beta = \frac{S_1 + S_2 - S_3 - S_4 + S_5 + S_6 - S_7 - S_8}{4I_0}$$

Furthermore, it is provable that, given a setting wherein the Polarizer 111 rotates and the Analyzer 115 is fixed, there are exactly 3 independent quantities that can be extracted from the ellipsometry measurements. This means that while it is possible to bin intensities differently and/or take different combinations of measured intensities, the final obtained quantities can be expressed using the signals $I_0$, $\alpha$ and $\beta$.

Symmetric Signals

A general idea of the present invention is to carry out measurements with more than one analyzer 115 angle. In the general grating case, as is described below, there are many ways to combine scattering intensities obtained at different Analyzer 115 angles in order to produce symmetric signals. The methods used in order to calculate the overlay for the azimuth-0 case, as described in the U.S. patent application Ser. No. 10/729,838, can be efficiently used with any of these combinations in order to calculate the overlay for the general grating case.

For example, in one proposed configuration, the Polarizer 111 rotates and two measurements are taken, one with the Analyzer 115 at an angle A and the other with the Analyzer 115 at the angle −A. Of course, any suitable number of Analyzer 115 angles may be utilized. The ellipsometry signals α and β, and the total reflected light intensity $I_0$, are recorded for a range of wavelengths and for the two Analyzer 115 angles. Given any wavelength of the polarized light, while the signals $I_0$, α and β by themselves do not have desired symmetry properties, the 6 obtained quantities α(A), α(−A), β(A), β(−A), $I_0$(A) and $I_0$(−A) can be combined into symmetric signals. In the case of 1D gratings with the incident beam of light parallel to the grating lines (the azimuth-90 case), the following expressions are examples of symmetric signals:

$I_0(A)+I_0(-A)$, $\alpha(A)I_0(A)+\alpha(-A)I_0(-A)$ and $\beta(A)I_0(A)-\beta(-A)I_0(-A)$ For normalized signals, the following can be used:

$$\frac{\alpha(A)I_0(A) + \alpha(-A)I_0(-A)}{I_0(A) + I_0(-A)}$$

and $$\frac{\beta(A)I_0(A) - \beta(-A)I_0(-A)}{I_0(A) + I_0(-A)}$$

Other methods of obtaining symmetric signals in the framework of RPRA ellipsometry are described below.

Anti-Symmetric Signals

It is also possible to construct anti-symmetric combinations of α(A), α(−A), β(A), β(−A), $I_0$(A) and $I_0$(−A), i.e. combinations that are odd functions of the shift between the top and bottom gratings. Examples of anti-symmetric signals for azimuth-90 gratings are:

$I_0(A)-I_0(-A)$, $$\alpha(A)I_0(A) - \alpha(-A)I_0(-A)$$

and $\beta(A)I_0(A) + \beta(-A)I_0(-A)$ which can be normalized as follows:

$$\frac{I_0(A) - I_0(-A)}{I_0(A) + I_0(-A)},$$

$$\frac{\alpha(A)I_0(A) - \alpha(-A)I_0(-A)}{I_0(A) + I_0(-A)}$$

and $$\frac{\beta(A)I_0(A) + \beta(-A)I_0(-A)}{I_0(A) + I_0(-A)}$$

Other methods of obtaining anti-symmetric signals in the framework of RPRA ellipsometry are described below.

In the case of 2D gratings, it is possible to construct symmetric and anti-symmetric functions of the shifts in the X direction, as well as symmetric and anti-symmetric functions of the shifts in the Y direction.

Anti-symmetric signals do contain overlay information. One possible use of the overlay information contained in anti-symmetric signals is to combine it with the information obtained from symmetric signals in order to enhance the precision and accuracy of the predicted overlay, as described below. Another possibility is to use only anti-symmetric signals to measure overlay. In the latter case, the required number of cells per target is smaller than that for symmetric signals, thereby reducing target size and MAM time. For example, in the case of 1D grating targets, one algorithm comprises a parameterization of the scatterometry signal as an expansion in terms of the shift:

$$R(v) = a + b \cdot \cos(2\pi v/p) + c \cdot \cos(4\pi v/p)$$

wherein v is the shift between the top and bottom gratings in a cell, and p is the grating pitch. This two-harmonics expansion is valid only if R is a symmetric signal. For each cell in the target, the shift v is a sum of a known intentional shift, which may differ from cell to cell, and the overlay, which is common to the cells in the target. The number of unknowns in this expression is four, comprising the three expansion coefficients and the overlay. Four measurements, taken from 4 cells, therefore suffice in order to measure the overlay.

If the signal is anti-symmetric, the two harmonics expansion is:

$$R(v) = b \cdot \sin(2\pi v/p) + c \cdot \sin(4\pi v/p)$$

Since the number of unknowns in the anti-symmetric case is only three, the total number of needed cells is reduced by one as compared to the symmetric case.

Figure 4A:
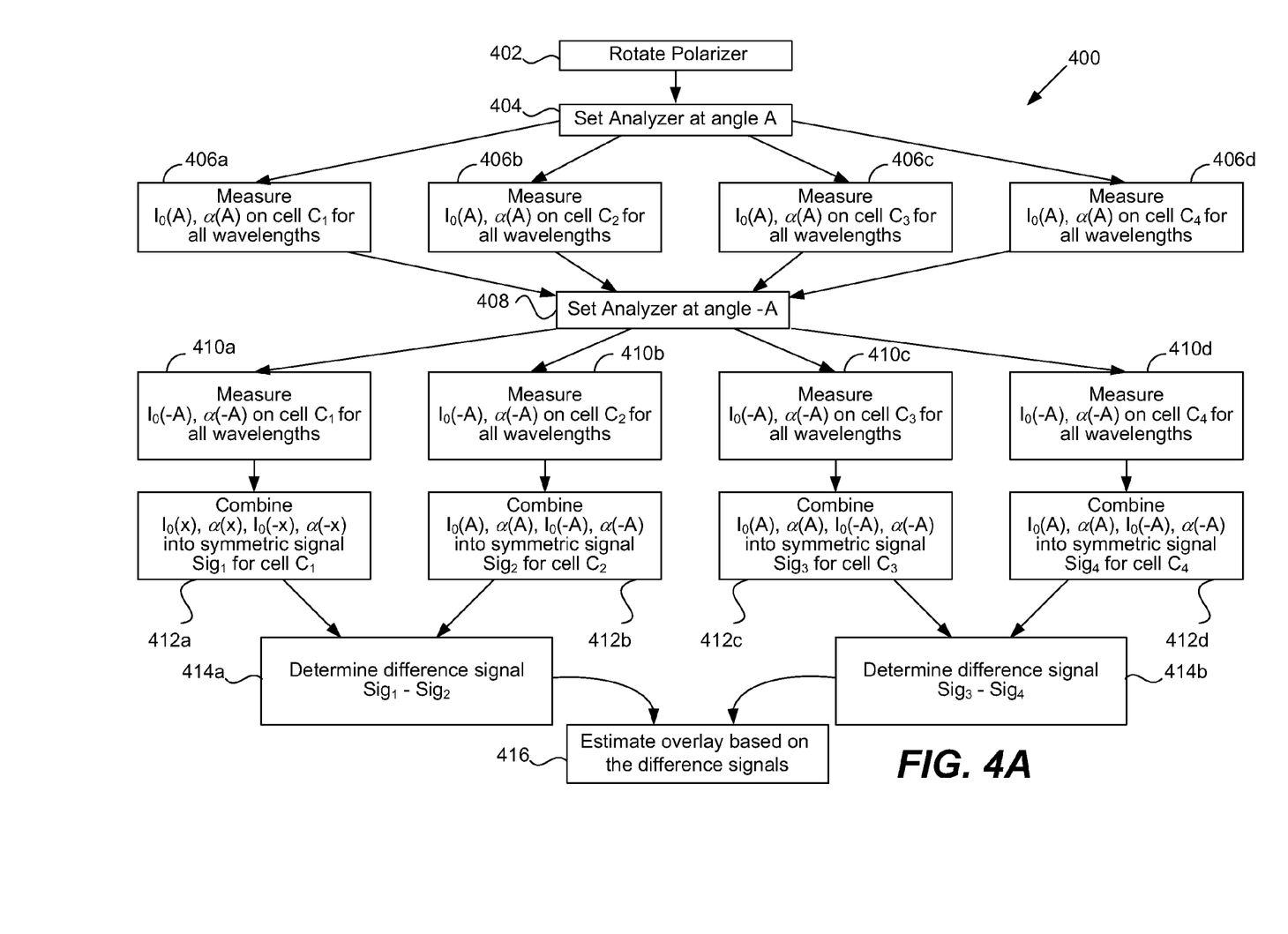
FIG. 4A is a flow diagram illustrating an example method for estimating overlay using an ellipsometry configuration, in accordance with an embodiment of the present invention.

FIG. 4A is a flow diagram illustrating an example method 400 for estimating overlay using an ellipsometry configuration in accordance with an embodiment of the present invention. In the example illustrated in FIG. 4A, the Polarizer (e.g., 111) is rotated in operation 402. The Analyzer (e.g., 115) is also set for a first angle A in operation 404. For the first cell $C_1$, $I_0(A)$ and $\alpha(A)$ are measured with the Analyzer set at angle A and for all wavelengths of the incident light in operation 406a. Similar measurements are made for the other three cells $C_2$~$C_4$ in operations 406b~d.

The Analyzer is then set to a second angle −A in operation 408. At operation 410a, $I_0(-A)$ and $\alpha(-A)$ are measured with the Analyzer at angle −A for cell $C_1$. Similar measurements are obtained for the cells $C_2$~$C_4$ in operations 410b~410d.

At operation 412a, the measured $I_0(A)$, $\alpha(A)$, $I_0(-A)$ and $\alpha(-A)$ for the first cell $C_1$ are combined into a symmetric signal $Sig_1$. At operations 412b, the measurements for the second cell $C_2$ are combined into a symmetric signal $Sig_2$, and the difference $Sig_1$-$Sig_2$ is determined at operation 414a. The measurements for cells $C_3$ and $C_4$ are also combined into symmetric signals $Sig_3$ and $Sig_4$ in operations 412c and 412d, respectively, and a difference $Sig_3$-$Sig_4$ is obtained in operation 414b. Finally, the overlay v is estimated based on the difference signals $Sig_1$-$Sig_2$ and $Sig_3$-$Sig_4$ in operation 416, as described, for example, in the U.S. patent application Ser. No. 10/729,838, which is incorporated herein by reference.

Note that the above method of FIG. 4A is exemplary. In general, the measured signals may be any of $I_0$, $\alpha$ and $\beta$, which may be combined into symmetric or anti-symmetric signals, as described above.

RPRA Ellipsometry

As explained above, up to three independent quantities can be measured with a rotating polarizer ellipsometer with the analyzer fixed at a given angle. Alternatively, rotating the Analyzer 115 results in a potentially different number of independent quantities. The actual number of extractable independent quantities depends on the ratio of the rotation rates of the Polarizer 111 and the Analyzer 115, and can be up to 9 independent measurable quantities.

For example, a Polarizer-to-Analyzer rotation rate ratio of 1:1 results in 5 independent measurable quantities, a 2:1 ratio results in 7, a 3:2 ratio results in 9, etc. However, generating symmetric or anti-symmetric signals from the extracted independent quantities may not always be feasible. For example, at a rotation rate ratio of 1:1 producing 5 independent quantities, there are exactly 3 symmetric and 2 anti-symmetric quantities that can be composed. On the other hand, while a rotation rate ratio of 2:1 produces 7 independent quantities, only 2 symmetric signals can be composed and the remaining quantities do not allow any additional composite signals with well-defined symmetries. Similarly, a ratio of 3:2 producing 9 quantities allows extraction of 6 symmetric and 3 anti-symmetric signals. An important point is that in these cases the symmetry property of the signal holds for the general grating case (not only for the azimuth-0 and azimuth-90 cases), and are also suitable for overlay measurements using 2D grating targets.

In general, when the Polarizer 111 and Analyzer 115 rotate at arbitrary rates, the intensity measured at the detector comprises components that vary according to the Polarizer 111 angle P and Analyzer 115 angle A. In general, the intensity I detected has the following form:

$$I = m_{11} + m_{12} \cdot \cos(2P) + m_{12} \cdot \sin(2P) + m_{21} \cdot \cos(2A) + m_{22} \cdot \cos(2A)\cos(2P) + m_{31} \cdot \sin(2A) + m_{32} \cdot \sin(2A)\cos(2P) + m_{33} \cdot \sin(2A)\sin(2P)$$

wherein the coefficients $m_{11}$, $m_{12}$, . . . , $m_{33}$ are the elements of the 3×3 Mueller matrix of the sample 113 under investigation, and RPRA ellipsometry is employed to measure the magnitude of these coefficients to extract overlay and CD information about the sample 113.

A special case of interest arises when the Polarizer 111 and Analyzer 115 rotate at the same rate and with equal angles of polarization, in which case:

$$I = a_1 + a_2 \cdot \cos(2P) + a_3 \cdot \sin(2P) + a_4 \cdot \cos(4P) + a_5 \cdot \sin(4A)$$

In this case, the coefficients $a_1$, . . . , $a_5$ are used to extract overlay information.

Figure 4B:
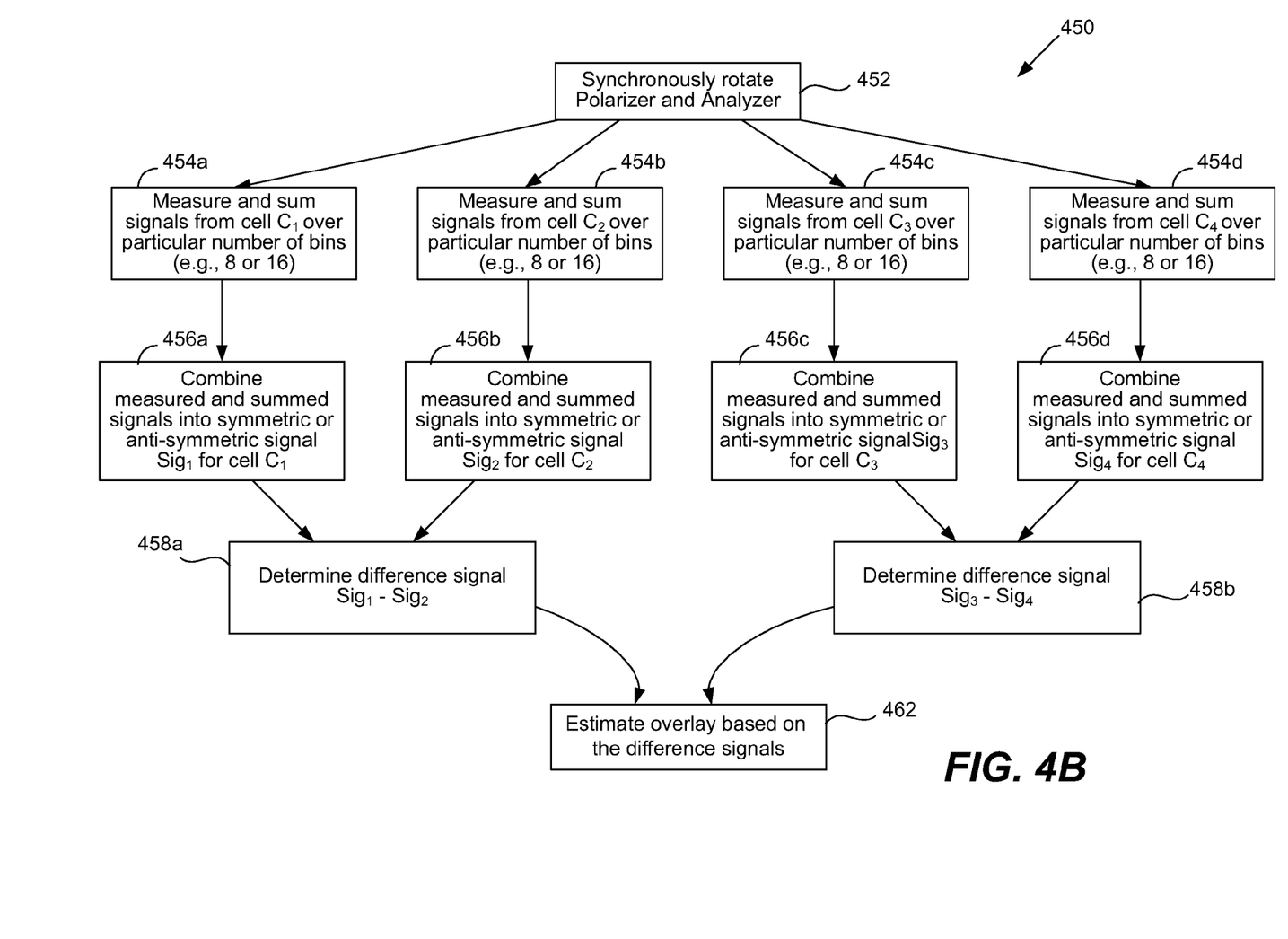
FIG. 4B is a flow diagram illustrating an example method for estimating overlay using an ellipsometry configuration in accordance with a second embodiment of the present invention.

In general, measurements can be triggered at specific intervals during the rotation of the Polarizer 111 and Analyzer 115. FIG. 4B is a flow diagram illustrating an example method 450 for estimating overlay using an ellipsometry configuration having a rotating, unfixed analyzer in accordance with an embodiment of the present invention. That is, in this embodiment the analyzer rotates, rather than being fixed at particular angles A and −A as described above with respect to FIG. 4A. Initially, both the polarizer and analyzer are rotated continuously and synchronously with respect to each other in operation 452. Signals from cell $C_1$ are then measured and summed over a particular number of bins (e.g., 8 or 16) in operation 454a. Signals from cells $C_2$, $C_3$, and $C_4$ are also measured and summed over a particular number of bins (e.g., 8 or 16) in operations 454b~d, respectively.

At operation 456a, the measured and summed signals for the first cell $C_1$ are combined into an anti-symmetric or symmetric signal $Sig_1$. At operation 456b, the measured and summed signals for the second cell $C_2$ are also combined into $Sig_2$, and the difference $Sig_1$-$Sig_2$ is determined at operation 458a. Similarly, the measured and summed signals for cells $C_3$ and $C_4$ are also combined into $Sig_3$ and $Sig_4$ in operations 456c and 456d, respectively. The difference $Sig_3$-$Sig_4$ is then obtained in operation 458b. Overlay is then determined based on the difference signals $Sig_1$-$Sig_2$ and $Sig_3$-$Sig_4$ in operation 462 as described herein.

The combination signals $Sig_1$~$Sig_4$ may be determined in any suitable manner so as to produce anti-symmetric or symmetric signals. If one rotates the polarizer and the analyzer synchronously with the same frequency and measures with 16 bins (intensities $S_1 \ldots S_{16}$), the following are examples of symmetric signals for a particular $cell_x$:

$$Sig_x = S_1 + S_2 + S_3 + S_4 + S_5 + S_6 + S_7 + S_8 + S_9 + S_{10} + S_{11} + S_{12} + S_{13} + S_{14} + S_{15} + S_{16}$$

$$Sig_x = S_1 - S_2 - S_3 + S_4 + S_5 - S_6 - S_7 + S_8 + S_9 - S_{10} - S_{11} + S_{12} + S_{13} - S_{14} - S_{15} + S_{16}$$

$$Sig_x = S_1 + S_2 - S_3 - S_4 - S_5 - S_6 + S_7 + S_8 + S_9 + S_{10} - S_{11} - S_{12} - S_{13} - S_{14} + S_{15} + S_{16}$$

while the following are examples of anti-symmetric signals:

$$Sig_x = S_1 + S_2 + S_3 + S_4 - S_5 - S_6 - S_7 - S_8 + S_9 + S_{10} + S_{11} + S_{12} - S_{13} - S_{14} - S_{15} - S_{16}$$

$$Sig_x = S_1 + S_2 - S_3 - S_4 + S_5 + S_6 - S_7 - S_8 + S_9 + S_{10} - S_{11} - S_{12} + S_{13} + S_{14} - S_{15} - S_{16}.$$

Synchronization between the Polarizer 111 and Analyzer 115 motors allows a phase control between the rotated Polarizer 111 and Analyzer 115. The Polarizer 111 and the Analyzer 115 may be rotated in the same direction or in opposite directions, and the phase difference between them can be made controllable, for example for a phase difference in the range of 0° to 180°. The phase difference may be used for light throughput optimization for specific quantities (elements of the Muller matrix).

In general, the ability to change the Polarizer-to-Analyzer rotation rate ratio "on the fly" introduces an additional system flexibility by allowing optimization of measurement performance for specific application, process layer and accuracy vs. wafer throughput tradeoffs. For example, the 1:1 rotation rate ratio provides high light throughput, while the 3:2 ratio allows to extract a larger number of Jones/Mueller matrix elements.

Measuring Profile Asymmetry

Anti-symmetric signals are useful for estimating the asymmetry of the profile of structures in a semiconductor wafer. For example, for a single layer 1D grating target (for example a scatterometry-CD target) with the incident beam parallel to the lines of the grating (azimuth-90), any anti-symmetric signal vanishes identically if the grating is symmetric with respect to reflection about the plane of incidence. Therefore, a finite value of an anti-symmetric signal is an indication of profile asymmetry in this case. While such a measurement is not quantitatively calibrated, it can be calibrated in a qualitative sense by carrying out a simulation of the scattering of light from a similar target with a pre-determined profile asymmetry. The measured value of an anti-symmetric signal can be normalized by the corresponding simulated value, yielding a qualitative relative measure of profile asymmetry. The per structure simulation performed for the purposes of this calibration process generally is not computing resource intensive, consuming for example no more than about one second of computing time, and needs only be carried out very rarely, namely when the process is changed. Therefore, the qualitative estimate of profile asymmetry can be obtained in a much shorter time than a scatterometry CD measurement and analysis.

It is also possible to carry out such a profile asymmetry measurement on more complex scatterometry overlay targets by algorithmically separating the profile asymmetry contribution to the signal from the contribution of the overlay. By way of example, this can be done by considering the two-harmonics expansion of the anti-symmetric signal. Note that this expansion does not comprise a constant term that is independent of the shift. However, an asymmetry in the profile of one of the gratings immediately introduces such a term, and the expansion will be:

$$R(v) = a + b \cdot \sin(2\pi v/p) + c \cdot \sin(4\pi v/p)$$

With four cells per target the three expansion coefficients, and thereby the overlay, can be evaluated. The value of the coefficient $\alpha$ is a measure of profile asymmetry. As described, this method cannot be implemented with symmetric signals, since the expansion of a symmetric signal comprises a finite constant term even when the grating profile is perfectly symmetric. Hence, it is the use of anti-symmetric signals which allows separation of the contribution of profile asymmetry to the signal from the contribution of the overlay. An advantage of this method is an increased accuracy in the overlay measurement, as well as the fact that two types of information are obtained simultaneously using a single target and a single measurement.

The described qualitative profile asymmetry measurement can be combined with scatterometry CD or profile measurement applications. While the present invention can be used to obtain information on the degree of asymmetry of a profile, a more detailed profile measurement can be carried out using methods such as those disclosed in U.S. patent application Ser. No. 10/729,838. Advantageously, when performing a more detailed profile measurement, the degree of asymmetry obtained using embodiments of the present invention can be used to increase efficiency of the detailed measurement. For example, prior knowledge of the degree of asymmetry of a given profile can be used to limit the search of profile shapes (in a library or in the regression sense) to a small number of relevant profiles. Since such degrees of asymmetry can be obtained using the techniques described above, embodiments of the present invention may help to increase the efficiency of more detailed profile measurements. Note that if layers have no asymmetry, differential signals will be indicative of the overlay shift. However, if layers have asymmetry, then layer asymmetry and overlay shift jointly contribute to the differential signal.

Other Configurations

Figure 5:
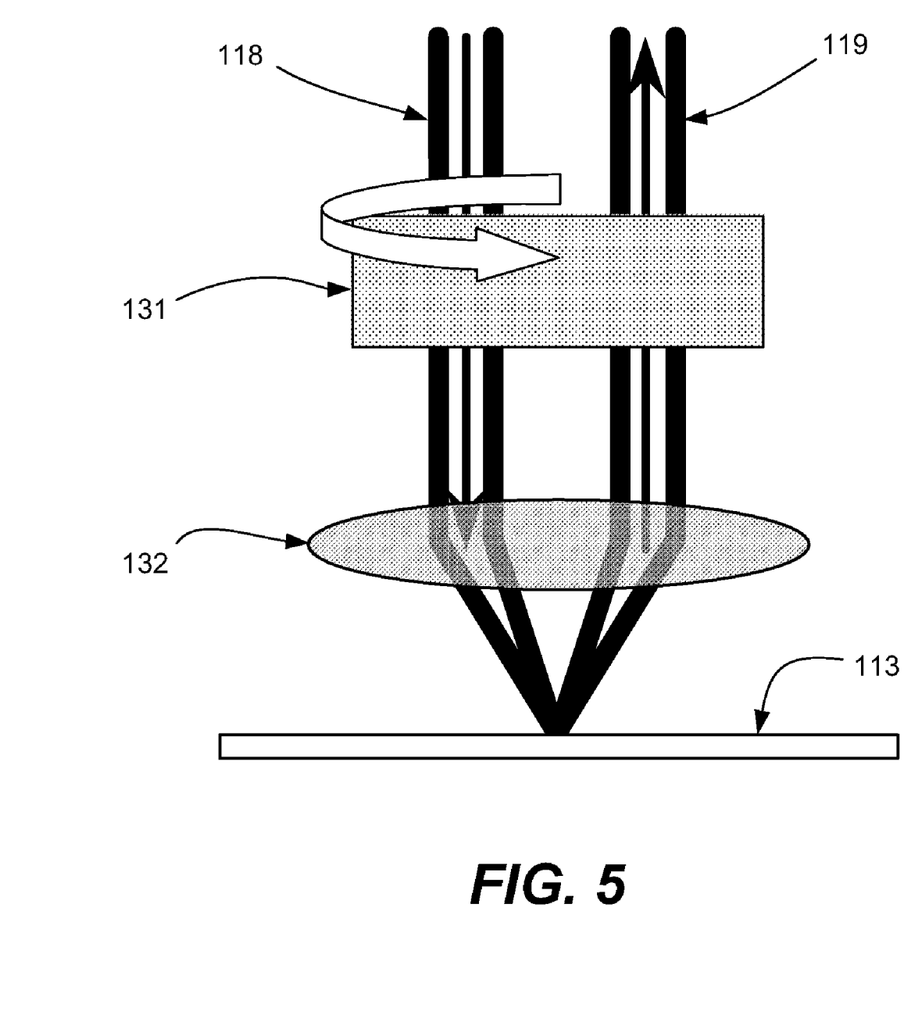
FIG. 5 illustrates an ellipsometry configuration, using refractive focusing optics and a Polarizer and Analyzer, in accordance with an alternative embodiment of the present invention.
Figure 6:
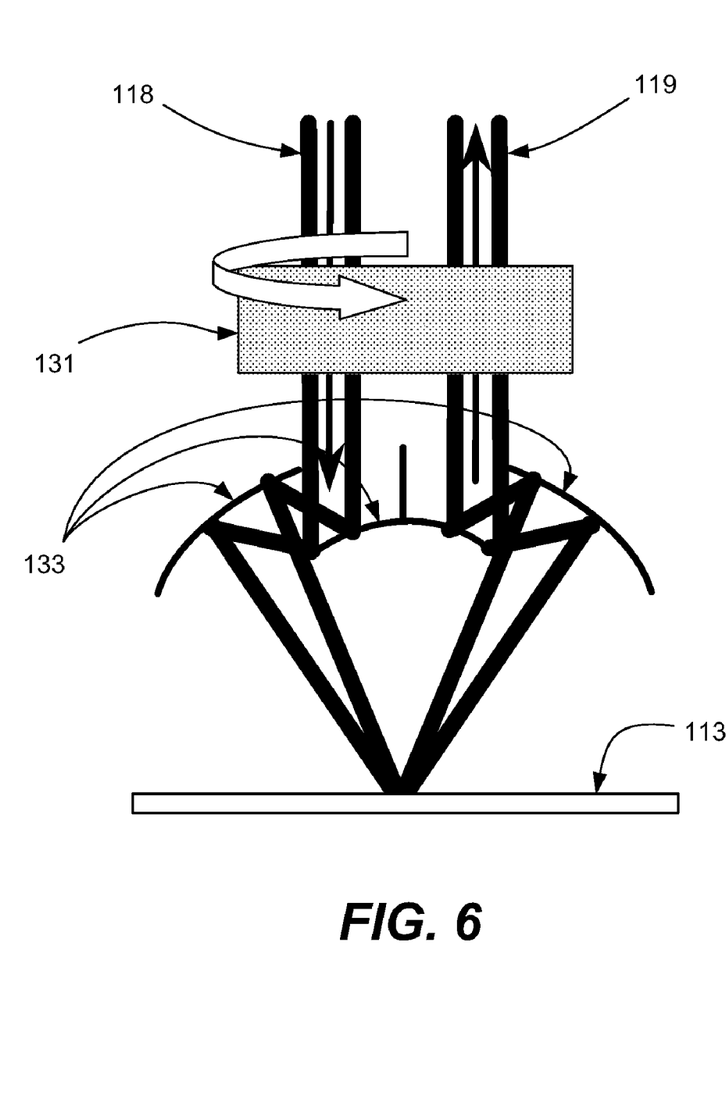
FIG. 6 illustrates an ellipsometry configuration, using reflective focusing optics and a Polarizer and Analyzer, in accordance with an alternative embodiment of the present invention.

In an optional embodiment of the present invention, the Polarizer 111 and the Analyzer 115 rotate with a 1:1 rotation rate ratio, but in opposite directions. This embodiment allows extraction of different Jones/Mueller matrix elements as well as a significant simplification of the hardware setup. In such an arrangement, as shown in FIGS. 5 and 6, the same rotating polarizer assembly 131 acts as a Polarizer for the incident beam and as an Analyzer for the reflected beam. This configuration has inherent perfect synchronization between the rotating Polarizer and Analyzer. Refractive or reflective focusing optics can be used in such an embodiment. FIG. 5 shows an embodiment using refractive focusing optics 132, and FIG. 6 shows an embodiment using reflective focusing optics 133.

Figure 7:
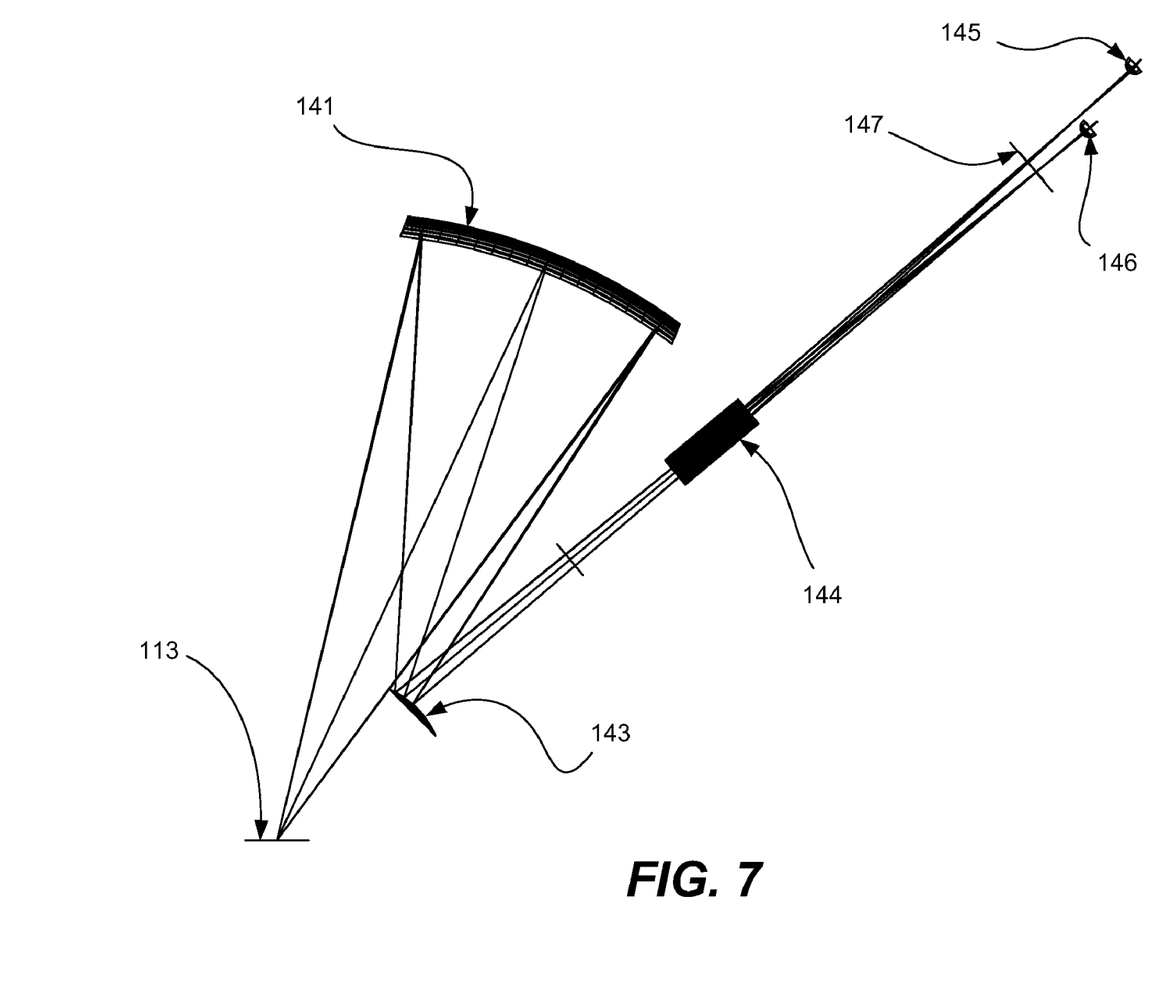
FIG. 7 illustrates an ellipsometry configuration wherein both polarization components of an analyzing beamsplitter prism are collected, in accordance with an alternative embodiment of the present invention.

In another optional embodiment of the present invention, an additional spectroscopic detection channel is added, both polarization components of an analyzing beamsplitter prism are collected, and their spectra are simultaneously recorded. FIG. 7 illustrates an example of such an embodiment. Light that is reflected from the sample 113 is collected by optics 141 and 143 into an analyzing prism 144. In principle, any analyzing prism form may be used, but a preferred embodiment comprises a Rochon prism of suitable material which produces an undeviated ordinary ray and an extra-ordinary ray. Since the analyzing prism 144 is chromatic for the extra-ordinary ray, a compensation prism following the analyzing prism 144 may be used, in order reverse the dispersion, and to "collapse" the light beam into a substantially achromatic state. This may be preferred for optimum light collection into a fiber or dispersing spectrometer devise. Note that FIG. 7 does not show such a compensation prism. The compensation wedge would be placed in the path of the extra-ordinary beam and just before the field lens 147. For ultraviolet-infrared (LW-IR) broad-band use, a fused silica or sapphire compensation prism may be used.

Light passing through the analyzing prism 144 splits into two rays: an ordinary ray and an extra-ordinary ray, which are collected at detectors 145 and 146, respectively. The polarizations of the two rays are orthogonal to each other. Therefore, collecting the two rays is equivalent to measuring with two Analyzer 115 angles having a difference of 90° between them. The analyzing prism 144 can be oriented in such a way that the two equivalent analyzer angles are +45° and −45°. This is the case of measuring at the two angles A and −A. This embodiment exploits the simultaneous detection of the ordinary and extra-ordinary rays from a fixed analyzer in a rotating Polarizer ellipsometer (or spectroscopic ellipsometer) optical configuration.

An advantage is that the amount of detected photons doubles, thereby improving overall performance (i.e. precision and/or throughput).

In addition to the above, embodiments of the present invention will employ a mechanism for an asymmetric (or anisotropic) numerical aperture of collection using a suitable collection aperture function. The collection aperture can be a top hat or "rect(x, y)" function, or any suitable apodizing profile, such as cos(x) cos(y), or combination of a rectangular function and attenuating profile (tapered function). Tailoring of the collection function in such a way as to adjust the weighting of the polar and azimuthal scattering components may be useful for some diffracting structures where limiting the amount of conical diffraction (or reflectance cross-terms) is desired.

Foregoing described embodiments of the invention are provided as illustrations and descriptions. They are not intended to limit the invention to precise form described. For example, many of the methods described herein in the context of ellipsometry apply equally to polarized reflectometry. Other variations and embodiments are possible in light of above teachings, and it is thus intended that the scope of invention not be limited by this Detailed Description, but rather by Claims following.

We claim:

1. An ellipsometry method for estimating overlay between a plurality of first structures in a first layer of a sample and a plurality of second structures in a second layer of the sample, the method comprising:
   providing a plurality of cells that each include a portion of the first and second structures, wherein each cell is designed to have an offset between its first and second structures portions;
   illuminating the cells with electromagnetic radiation using a rotating polarizer;
   obtaining measurements with an analyzer set at a plurality of polarization angles, wherein the measurements include reflected radiation intensities with the analyzer set at the plurality of polarization angles;
   combining the measurements into combinational signals for each of the cells so that the combinational signals are even or odd functions of a total shift between the first and second structures; and
   estimating and storing any overlay error between the first structures and the second structures based on the combinational signals.

2. The method of claim 1, wherein the measurements are obtained with a continuously rotating analyzer.

3. The method of claim 2, wherein the analyzer rotates in the same direction as the polarizer.

4. The method of claim 2, wherein the analyzer rotates in the opposite direction of the polarizer.

5. The method of claim 2, wherein stepper motors or servo motors are used to rotate the polarizer and the analyzer.

6. The method of claim 5, wherein synchronization between motors allows a rotation phase control between the polarizer and the analyzer, and wherein the analyzer and the polarizer are rotated in the same direction or in opposite directions.

7. The method of claim 2, wherein the ratio between the rotation rates of the polarizer and the analyzer is adjustable.

8. The method of claim 2, wherein the polarizer and analyzer form a element that rotate together.

9. The method of claim 1, wherein the cells include three or cells and the combinational are each odd functions of the total shift between the first and second structures.

10. The method of claim 1, wherein the cells include four or cells and the combinational signals are each even functions of the total shift between the first and second structures.

11. The method of claim 1, wherein the estimating any overlay error comprises:
   determining a first difference signal $Sig_1 - Sig_2$ between a first combinational signal from a first cell and a second combinational signal from a second cell;
   determining a second difference signal $Sig_3 - Sig_4$ between a third combinational signal from a third cell and a fourth combinational signal from a fourth cell;
   determining any overlay error by performing a linear approximation based on the first and second difference signals.

12. The method of claim 1, wherein the measurements comprise one or more elements of the Jones matrix or the Mueller matrix of the sample.

13. The method of claim 1, wherein the sample is in a semiconductor wafer, and the first and second plurality of structures comprise semiconductor devices.

14. The method of claim 1, wherein the plurality of angles consist of a first angle A and a second angle −A and the measurements are obtained with the analyzer at the angles A and −A.

15. The method of claim 1, wherein each measurement comprises a sum of measurements taken over a range of specific ones of the plurality of angles.

16. The method of claim 15, wherein there are eight measurement sums that are obtained over eight different angle ranges.

17. The method of claim 15, wherein there are sixteen measurement sums that are obtained over sixteen different angle ranges.

18. The method of claim 1, wherein the measurements are obtained by using the ordinary and extra-ordinary beams from a Rochon prism analyzer to obtain signals from two analyzer angles simultaneously.

19. A system for estimating overlay between a plurality of first structures in a first layer of a sample and a plurality of second structures in a second layer of the sample, comprising:
    an ellipsometry module for:
        illuminating the cells with electromagnetic radiation using a rotating polarizer;
        obtaining measurements with an analyzer set at a plurality of polarization angles, wherein the measurements include reflected radiation intensities with the analyzer set at the plurality of polarization angles; and
        combining the measurements into combinational signals for each of the cells so that the combinational signals are even or odd functions of a total shift between the first and second structures; and
    a processor operable for estimating any overlay error between the first structures and the second structures based on the combinational signals.

20. The system of claim 19, wherein the measurements are obtained with a continuously rotating analyzer.

21. The system of claim 20, wherein the polarizer and analyzer form a same element that rotate together.

22. The system of claim 19, wherein the cells include three or more cells and the combinational signals are each odd functions of the total shift between the first and second structures.

23. The system of claim 19, wherein the cells include four or more cells and the combinational signals are each even functions of the total shift between the first and second structures.

24. The method of claim 19, wherein the estimating any overlay error comprises:
    determining a first difference signal $Sig_1-Sig_2$ between a first combinational signal from a first cell and a second combinational signal from a second cell;
    determining a second difference signal $Sig_3-Sig_4$ between a third combinational signal from a third cell and a fourth combinational signal from a fourth cell;
    determining any overlay error by performing a linear approximation based on the first and second difference signals.

25. An ellipsometry method for measuring profile asymmetry of a structure of a sample, the method comprising:
    (a) illuminating a structure with electromagnetic radiation using a rotating polarizer;
    (b) obtaining a plurality of measurements with an analyzer set at a plurality of polarization angles, wherein the measurements include reflected radiation intensities with the analyzer set at the plurality of polarization angles;
    (c) combining the measurements into a combinational signal so that the combinational signals is an odd functions; and
    (d) determining a degree of profile asymmetry of the structure based on the combinational signal.

26. The method of claim 25, wherein operations (a) through (d) are performed for a plurality of cells that each include a portion of a first structure on a first layer and a second structure on a second layer and wherein each cell is designed to have an offset between its first and second structures, and wherein determining the degree of profile asymmetry comprises separating a contribution of profile asymmetry to the measurements from a contribution of overlay to the measurements.

27. The method of claim 26, further comprising:
    estimating any overlay error between the first structures and the second structures based on the signals and the determined profile asymmetry.

* * * * *

UNITED STATES PATENT AND TRADEMARK OFFICE
CERTIFICATE OF CORRECTION

PATENT NO. : 7,277,172 B2  Page 1 of 1
APPLICATION NO. : 11/325872
DATED : October 2, 2007
INVENTOR(S) : Kandel et al.

It is certified that error appears in the above-identified patent and that said Letters Patent is hereby corrected as shown below:

In the Title Page:

In the (75) Inventors section, change "Shakar Krishnan" to --Shankar Krishnan--.

In the Claims:

Col. 12 in line 45 claim 8, after "a" insert --same--.

Col. 12 in line 47 claim 9, after "or" insert --more--.

Col. 12 in line 47 claim 9, after "combinational" insert --signals--.

Col. 12 in line 50 claim 10, after "or" insert --more--.

Signed and Sealed this

Seventeenth Day of June, 2008

JON W. DUDAS
*Director of the United States Patent and Trademark Office*